United States Patent
Sager et al.

(10) Patent No.: US 7,605,328 B2
(45) Date of Patent: *Oct. 20, 2009

(54) PHOTOVOLTAIC THIN-FILM CELL PRODUCED FROM METALLIC BLEND USING HIGH-TEMPERATURE PRINTING

(75) Inventors: Brian M. Sager, Menlo Park, CA (US); Martin R. Roscheisen, San Francisco, CA (US)

(73) Assignee: Nanosolar, Inc., San Jose, CA (US)

(*) Notice: Subject to any disclaimer, the term of this patent is extended or adjusted under 35 U.S.C. 154(b) by 620 days.

This patent is subject to a terminal disclaimer.

(21) Appl. No.: 10/836,307

(22) Filed: Apr. 30, 2004

(65) Prior Publication Data

US 2005/0183768 A1 Aug. 25, 2005

Related U.S. Application Data

(63) Continuation-in-part of application No. 10/782,017, filed on Feb. 19, 2004.

(51) Int. Cl.
*H01L 31/00* (2006.01)
*H01L 21/00* (2006.01)
*B05D 5/12* (2006.01)

(52) U.S. Cl. ............... 136/265; 136/262; 136/264; 427/74; 427/76

(58) Field of Classification Search ........... 136/262, 136/264, 265; 428/558; 427/74, 76, 180–206, 427/356–357, 430.1, 428.06, 446–456, 123, 427/126.1, 431
See application file for complete search history.

(56) References Cited

U.S. PATENT DOCUMENTS

| | | | |
|---|---|---|---|
| 3,423,301 A | 1/1969 | Sterns | 204/105 |
| 3,586,541 A | 6/1971 | Chamberlin | 136/206 |
| 3,966,568 A | 6/1976 | Crossley et al. | 205/564 |
| 4,191,794 A | 3/1980 | Shirland et al. | 438/80 |
| 4,192,721 A | 3/1980 | Fawcett et al. | 205/229 |
| 4,404,422 A | 9/1983 | Green et al. | 136/255 |
| 4,522,663 A | 6/1985 | Ovshinsky et al. | 148/403 |
| 4,536,607 A | 8/1985 | Wiesmann | 136/249 |

(Continued)

FOREIGN PATENT DOCUMENTS

DE 2741954 3/1979

(Continued)

OTHER PUBLICATIONS

U.S Appl. No. 60/548,297, "Low Cost Deposition Approaches for Semiconductor Film Growth", filed Mar. 1, 2004.*

(Continued)

*Primary Examiner*—Jeffrey T. Baron

(57) ABSTRACT

The metallic components of a IB-IIIA-VIA photovoltaic cell active layer may be directly coated onto a substrate by using relatively low melting point (e.g., less than about 500° C.) metals such as indium and gallium. Specifically, CI(G)S thin-film solar cells may be fabricated by blending molten group IIIA metals with solid nanoparticles of group IB and (optionally) group IIIA metals. The molten mixture may be coated onto a substrate in the molten state, e.g., using coating techniques such as hot-dipping, hot microgravure and/or air-knife coating. After coating, the substrate may be cooled and the film annealed, e.g., in a sulfur-containing or selenium-containing atmosphere.

44 Claims, 1 Drawing Sheet

U.S. PATENT DOCUMENTS

| | | | |
|---|---|---|---|
| 4,622,432 A | 11/1986 | Yamazaki | 136/246 |
| 4,642,140 A | 2/1987 | Noufi et al. | 438/95 |
| 4,677,250 A | 6/1987 | Barnett et al. | 136/258 |
| 4,806,436 A | 2/1989 | Tada et al. | 428/629 |
| 4,940,604 A | 7/1990 | Suyama et al. | 427/76 |
| 5,013,464 A | 5/1991 | Sugimura et al. | |
| 5,045,409 A | 9/1991 | Eberspacher et al. | 428/620 |
| 5,078,804 A | 1/1992 | Chen et al. | 136/260 |
| 5,141,564 A | 8/1992 | Chen et al. | 136/258 |
| 5,244,509 A | 9/1993 | Arao et al. | 136/259 |
| 5,277,786 A | 1/1994 | Kawakami | 205/124 |
| 5,286,306 A | 2/1994 | Menezes | 136/249 |
| 5,356,839 A | 10/1994 | Tuttle et al. | 438/479 |
| 5,401,573 A | 3/1995 | Babel et al. | 428/336 |
| 5,419,781 A | 5/1995 | Hamakawa et al. | 136/244 |
| 5,436,204 A | 7/1995 | Albin et al. | 438/488 |
| 5,441,897 A | 8/1995 | Noufi et al. | 438/95 |
| 5,445,847 A | 8/1995 | Wada et al. | 427/74 |
| 5,538,903 A | 7/1996 | Aramoto et al. | 438/94 |
| 5,567,469 A | 10/1996 | Wada et al. | 427/74 |
| 5,578,503 A | 11/1996 | Karg et al. | 438/95 |
| 5,626,688 A | 5/1997 | Probst et al. | 136/265 |
| 5,633,033 A | 5/1997 | Nishitani et al. | 427/8 |
| 5,677,250 A | 10/1997 | Knapp | 501/14 |
| 5,728,231 A | 3/1998 | Negami et al. | 148/33 |
| 5,730,852 A | 3/1998 | Bhattacharya et al. | 205/192 |
| 5,925,228 A | 7/1999 | Panitz et al. | 204/484 |
| 5,945,217 A | 8/1999 | Hanrahan | |
| 5,985,691 A | 11/1999 | Basol et al. | 438/95 |
| 5,994,163 A | 11/1999 | Bodegard et al. | 438/84 |
| 6,022,487 A | 2/2000 | Daume et al. | |
| 6,107,562 A | 8/2000 | Hashimoto et al. | |
| 6,121,541 A | 9/2000 | Arya | 136/255 |
| 6,124,039 A | 9/2000 | Goetz et al. | 428/457 |
| 6,124,041 A | 9/2000 | Aoude et al. | 428/472 |
| 6,126,740 A | 10/2000 | Schulz et al. | 117/4 |
| 6,127,202 A * | 10/2000 | Kapur et al. | 438/47 |
| 6,150,022 A | 11/2000 | Coulter | |
| 6,228,904 B1 | 5/2001 | Yadav et al. | 523/210 |
| 6,268,014 B1 | 7/2001 | Eberspacher et al. | 427/74 |
| 6,323,417 B1 | 11/2001 | Gillespie et al. | 136/262 |
| 6,344,272 B1 | 2/2002 | Oldenburg et al. | |
| 6,454,886 B1 | 9/2002 | Martin et al. | 149/2 |
| 6,472,459 B2 | 10/2002 | Morales et al. | 524/439 |
| 6,518,086 B2 | 2/2003 | Beck et al. | |
| 6,593,690 B1 * | 7/2003 | McCormick et al. | 313/506 |
| 6,641,898 B2 * | 11/2003 | Yazaki et al. | 428/209 |
| 6,685,986 B2 | 2/2004 | Oldenburg et al. | |
| 6,897,603 B2 | 5/2005 | Mao et al. | |
| 6,974,976 B2 | 12/2005 | Hollars | 257/184 |
| 7,144,627 B2 | 12/2006 | Halas et al. | |
| 2002/0006470 A1 | 1/2002 | Eberspacher et al. | 427/216 |
| 2002/0132045 A1 | 9/2002 | Halas et al. | |
| 2002/0160195 A1 | 10/2002 | Halas et al. | |
| 2002/0187347 A1 | 12/2002 | Halas et al. | |
| 2003/0051664 A1 | 3/2003 | Stanbery | |
| 2003/0052382 A1 | 3/2003 | Stanbery | |
| 2003/0052391 A1 | 3/2003 | Stanbery | |
| 2003/0054582 A1 | 3/2003 | Stanbery | |
| 2003/0054661 A1 | 3/2003 | Stanbery | |
| 2003/0054662 A1 | 3/2003 | Stanbery | |
| 2003/0054663 A1 | 3/2003 | Stanbery | |
| 2003/0192584 A1 | 10/2003 | Montello et al. | |
| 2003/0205270 A1 | 11/2003 | Stanbery | |
| 2003/0211646 A1 | 11/2003 | Stanbery | |
| 2004/0144419 A1 | 7/2004 | Fix et al. | 136/252 |
| 2004/0214001 A1 | 10/2004 | Oldenburg et al. | |
| 2004/0219730 A1 | 11/2004 | Basol | 438/200 |
| 2005/0022747 A1 | 2/2005 | Stanbery | |
| 2005/0035983 A1 | 2/2005 | Cruchon-Dupeyrat et al. | |
| 2005/0058587 A1 | 3/2005 | Wagner | |
| 2005/0150789 A1 | 7/2005 | Crane | |
| 2005/0175836 A1 | 8/2005 | Kuehnle et al. | |
| 2005/0183767 A1 | 8/2005 | Yu et al. | 136/263 |
| 2005/0183768 A1 | 8/2005 | Roscheisen et al. | |
| 2005/0186342 A1 | 8/2005 | Sager et al. | 427/248.1 |
| 2005/0186805 A1 | 8/2005 | Stanbery | |
| 2005/0194036 A1 * | 9/2005 | Basol | 136/252 |
| 2005/0194038 A1 | 9/2005 | Brabec et al. | |
| 2005/0202589 A1 | 9/2005 | Basol | |
| 2005/0235869 A1 | 10/2005 | Cruchon-Dupeyrat et al. | |
| 2005/0247340 A1 | 11/2005 | Zeira et al. | |
| 2005/0266600 A1 | 12/2005 | Basol | |
| 2005/0268962 A1 | 12/2005 | Gaudiana et al. | |
| 2005/0272263 A1 | 12/2005 | Brabec et al. | |
| 2006/0054506 A1 | 3/2006 | Natan et al. | |
| 2006/0099146 A1 | 5/2006 | Chow et al. | |
| 2006/0121701 A1 | 6/2006 | Basol | |
| 2006/0134505 A1 | 6/2006 | Wang et al. | |
| 2006/0159922 A1 | 7/2006 | O'Keefe | |
| 2006/0165911 A1 | 7/2006 | Basol | |
| 2006/0178012 A1 | 8/2006 | Basol | |
| 2006/0189155 A1 | 8/2006 | Basol | |
| 2006/0192955 A1 | 8/2006 | Jorgenson et al. | |
| 2006/0207644 A1 | 9/2006 | Robinson et al. | |
| 2006/0251874 A1 | 11/2006 | McClure et al. | |
| 2007/0044834 A1 | 3/2007 | Berke et al. | |
| 2007/0092648 A1 | 4/2007 | Van Duren et al. | |
| 2007/0093006 A1 | 4/2007 | Basol | |
| 2007/0093059 A1 | 4/2007 | Basol | |
| 2007/0111367 A1 | 5/2007 | Basol | |
| 2007/0145507 A1 | 6/2007 | Basol | |
| 2007/0163383 A1 | 7/2007 | Van Duren et al. | |
| 2007/0163637 A1 | 7/2007 | Robinson et al. | |
| 2007/0163638 A1 | 7/2007 | Van Duren et al. | |
| 2007/0163639 A1 | 7/2007 | Robinson et al. | |
| 2007/0163640 A1 | 7/2007 | Van Duren et al. | |
| 2007/0163642 A1 | 7/2007 | Van Duren et al. | |
| 2007/0163643 A1 | 7/2007 | Van Duren et al. | |
| 2007/0163644 A1 | 7/2007 | Van Duren et al. | |
| 2007/0166453 A1 | 7/2007 | Van Duren et al. | |
| 2007/0166964 A1 | 7/2007 | Basol | |
| 2007/0169809 A1 | 7/2007 | Van Duren et al. | |
| 2007/0169810 A1 | 7/2007 | Van Duren et al. | |
| 2007/0169811 A1 | 7/2007 | Van Duren et al. | |
| 2007/0169812 A1 | 7/2007 | Robinson et al. | |
| 2007/0169813 A1 | 7/2007 | Robinson et al. | |
| 2007/0178620 A1 | 8/2007 | Basol | |
| 2008/0121277 A1 | 5/2008 | Robinson et al. | |
| 2008/0124831 A1 | 5/2008 | Robinson et al. | |

FOREIGN PATENT DOCUMENTS

| | | |
|---|---|---|
| EP | 793277 | 9/1997 |
| JP | 61244004 | 10/1986 |
| JP | 62-89369 | 4/1987 |
| JP | 63-249379 | 10/1988 |
| JP | 2001-044464 | 2/2001 |
| KR | 2005119705 A | 12/2005 |
| WO | WO 02/084708 | 10/2002 |
| WO | WO 03/007386 | 1/2003 |
| WO | WO 03/043736 A2 | 5/2003 |

OTHER PUBLICATIONS

U.S. Appl. No. 10/782,017 entitled "Solution-Based Fabrication of Photovoltaic Cell", filed Feb. 19, 2004.

S. L. Castro et al. "Nanocrystalline Chalcopyrite Materials ($CuInS_2$ and $CuInSe_2$) via Low-Temperature Pyrolysis of Molecular Single-Source Precursors" *Chem. Mater*, vol. 15, pp. 3142-3147, 2003.

B. A. Ridley et al, "All-Inorganic Field Effect Transistors Fabricated by Printing" in *Science*, vol. 286, pp. 746-749, Oct. 22, 1999.

J. Zhu, et al, "General Sonochemical Method for the Preparation of Nanophasic Selenides: Synthesis of ZnSe Nanoparticles" in *Chem. Mater*. 2000, vol. 12, pp. 73-78.

B. Li, et al. "Synthesis by a Solvothermal Route and Characterization of CuInSe2 Nanowhiskers and Nanoparticles" in *Advanced Materials*, vol. 11, No. 17, pp. 1456-1459, 1999, Wiley-VCH Verlag GmbH.

P. Sen, et al. "Preparation of Cu, Ag, Fe and Al nanoparticles by the exploding wire technique" in *Proc. Indian Acad. Sci. (Chem. Sci)*, vol. 115, Nos. 5 & 6, pp. 499-508, Oct.-Dec. 2003, Indian Academy of Sciences.

M. A. Malik et al. "A Novel Route for the Preparation of CuSe and CuInSe2 Nanoparticles"in *Advanced Materials*, vol. 11, No. 17, pp. 1441-1444, Wiley-VCH Verlag GmbH, Weinheim.

K. K. Banger et al. "Synthesis and Characterization of the First Liquid Single-Source Precursors for the Deposition of Ternary Chalcopyrite (CuInS2) Thin Film Materials" in *Chem. Mater.*, vol. 13, 3827-3829, 2001, American Chemical Society.

Vijay K. Kapur, Ashish Bansal, Phucan Le, and Omar I. Asensio, Non-vacuum processing of $CuIn_{1-x}Ga_xSe_2$ solar cells on rigid and flexible substrates using nanoparticles precursor inks, Thin Solid Films, 2003, 53-57, vol. 431-432, Elsevier Publishing Company, Amsterdam.

Markus E. Beck, and Michael Cocivera, Thin-film copper indium diselenide prepared by selenization of copper indium oxide formed by spray pyrolysis, Thin Solid Films, 1996, 71-82, vol. 272, Elsevier Publishing Company, Amsterdam.

C. Eberspacher, K. Pauls, and J. Serra, Non-vacuum processing of CIGS solar cells, UNISUN, 223-224, 2001, Newbury Park, CA.

T. Arita, N. Suyama, Y. Kita, S. Kitamura, T. Hibino, H. Takada, K. Omura, N. Ueno, and M. Murozono, $CuInSe_2$ films prepared by screen-printing and sintering method, 1988, IEEE.

Douglas L. Schulz, Calvin J. Curtis, Rebecca A. Flitton, Holm Wiesner, James Keane, Richard J. Matson, Kim M. Jones, Philip A. Parilla, Rommel Noufi, and David S. Ginley, Cu-In-Ga-Se Nanoparticle Colloids as Spray Deposition Precursors for Cu(In, Ga)Se2 Solar Cell Materials, Journal of Electronic Materials, 1998, 433-437, vol. 27, No. 5, Minerals Metals & Materials Society : USA.

Claire J. Carmalt, Daniel E. Morrison, and Ivan P. Parkin, Solid-state and solution phase metathetical synthesis of copper indium chalcogenides, Journal of Materials Chemistry, 1998, 2209-2211, vol. 8, No. 10, Royal Society of Chemistry (Great Britain).

Shixing Weng and Michael Cocivera, Preparation of copper indium diselenide by selenization of copper indium oxide, Journal of Applied Physics, Aug. 1, 1993, 2046-2052, vol. 74, No. 3, American Institute of Physics, New York.

G.. Norsworthy, C.R. Leidholm, A. Halani, V.K. Kapur, R. Roe, B.M. Basol, and R. Matson, CIS film growth by metallic ink coating and selenization, Solar Energy Materials & Solar Cells, 2000, 127-134, vol. 60, Elsevier Sciences, Amsterdam : Netherlands.

Chris Eberspacher, Chris Fredric, Karen Pauls, and Jack Serra, Thin-filme CIS alloy PV materials fabricated using non-vacuum, particles-based techniques, Thin Solid Films, 2001, 18-22, vol. 387, Elsevier Publishing Company, Amsterdam.

C. Eberspacher, K. L. Pauls, and C. V. Fredric, Improved processes for forming $CuInSe_2$ films, UNISUN, 1-4, Newbury Park, CA.

Chris Eberspacher, Karen L. Pauls, and John P. Serra, Non-vacuum thin-film CIGS modules, Materials Research Society Symposia Proceedings, 2003, B8.27.1-B8.27.6, vol. 763, Materials Research Society, Warrendale, PA.

M. Kaelin, D. Rudmann, F. Kurdesau, T. Meyer, H. Zogg, A.N. Tiwari, CIS and CIGS layers from selenized nanoparticle precursors, Thin Solid Films, 2003, 58-62, vol. 431-432, Elsevier Science, Amsterdam : Netherlands.

M. Kaelin, H. Zogg, A.N. Tiwari, O. Wilhelm, S.E. Pratsinis, T. Meyer, and A. Meyer, Electrosprayer and selenized Cu/In metal particle films, Thin Solid Films, 2004, 391-396, vol. 457, Elsevier Science, Amsterdam : Netherlands.

R.P. Raffaelle, J.G. Mantovani, S.G. Bailey, A.F. Hepp, E.M. Gordon and R. Haraway, Electrodeposited $CuInSe_2$ thin film junctions, Prepared for the 1997 Fall meeting sponsored by the Materials Research Society, Dec. 1-5, 1997, Boston, MA.

K.T. Ramakrishna Reddy, R.B.V. Chalapathy, M.A. Slifkin, A.W. Weiss, And R.W. Miles, Photoacousstic spectroscopy of sprayed $CuGa_xIn_{1-x}Se_2$ thin films, Thin Solid Films, 2001, 205-207, vol. 387, Elsevier Science, Amsterdam : Netherlands.

C. Guillen, and J. Herrero, Recrystallization and components redistribution processes in electrodeposited $CuInSe_2$ thin films, Thin Solid Films, 2001, 57-59, vol. 387, Elsevier Science, Amsterdam : Netherlands.

K.T.L. De Silva, W.A.A. Priyantha, J.K.D.S Jayanetti, B.D. Chithrani, W. Siripala, K. Blake, and I.M. Dharmadasa, Electrodeposition and characterization of $CuInSe_2$ for applications in thin film solar cells, Thin Solid Films, 2001, 158-163, vol. 382, Elsevier Science, Amsterdam : Netherlands.

A. G. Munoz, S. B. Saidman, and J. B. Bessone, Electrodeposition of Indium onto Vitreous Carbon from Acid Chloride Solutions, Journal of The Electrochemical Society, 1999, 2123-2130, vol. 146, No. 6, Electrochemical Society Inc : USA.

D. Padhi, J. Yahalom, S. Gandikota, and G. Dixit, Planarization of Copper Thin Films by Electropolishing in Phosphoric Acid for ULSI Applications, Journal of the Electrochemical Society, 2003, G10-G14, vol. 150, No. 1, Electrochemical Society Inc : USA.

George L. Schnable and John G. Javes, Electrodeposition of Molten Low-Melting Metals and Alloys from Fused-Salt Systems, Electrochemical Technology, Jul.-Aug. 1964, 201-206, Electrochemical Society, Manchester, N.H.

George L. Schnable, Electrodeposition of Molten Metals and Alloys from Glycerine Solutions, Jounal of the Electrochemical Society, Oct. 1961, 964-969, vol. 108, No. 10, Electrochemical Society Inc : USA.

William M. Saltman and Norman H. Nachtrieb, The Electrochemistry of Gallium, Journal of the Electrochemical Society, Mar. 1953, 126-130, vol. 100, No. 3, Electrochemical Society Inc: USA.

Marianna Kemell, Heini Saloniemi, Mikko Ritala, and Markku Leskela, Electrochemical Quartz Crystal Microbalance Study of the Electrodeposition Mechanisms of $CuInSe_2$ Thin Films, Journal of The Electrochemical Society, 2001, C110-C118, vol. 148, No. 2, Electrochemical Society: USA.

A. Kampmann, P. Cowache, D. Lincot, and J. Vedel, Juction Formation Studies of One-Step Electrodeposited $CuInSe_2$ on CdS, Journal of The Electrochemical Society, 1999, 150-155, vol. 146, No. 1, Royal Society of Chemistry (Great Britian).

C. Eberspacher, K. Pauls, and J. Serra, Non-vacuum processing of CIGS solar cells, UNISUN, pp. 1-5, 2003 Newbury Park, CA.

U.S. Appl. No. 11/933,136, filed Oct. 31, 2007 titled "Solution-based Fabrication of Photovoltaic Cell".

U.S. Appl. No. 11/933,255, filed Oct. 31, 2007 titled "Solution-based Fabrication of Photovoltaic Cell".

U.S. Appl. No. 11/933,285, filed Oct. 31, 2007 titled "Solution-based Fabrication of Photovoltaic Cell".

U.S. Appl. No. 11/933,315, filed Oct. 31, 2007 titled "Solution-based Fabrication of Photovoltaic Cell".

U.S. Appl. No. 11/933,322, filed Oct. 31, 2007 titled "Solution-based Fabrication of Photovoltaic Cell".

U.S. Appl. No. 11/933,338, filed Oct. 31, 2007 titled "Solution-based Fabrication of Photovoltaic Cell".

U.S. Appl. No. 11/933,357, filed Oct. 31, 2007 titled "Solution-based Fabrication of Photovoltaic Cell".

U.S. Appl. No. 11/933,375, filed Oct. 31, 2007 titled "Solution-based Fabrication of Photovoltaic Cell".

U.S. Appl. No. 11/933,400, filed Oct. 31, 2007 titled "Solution-based Fabrication of Photovoltaic Cell".

U.S. Appl. No. 11/933,407, filed Oct. 31, 2007 titled "Solution-based Fabrication of Photovoltaic Cell".

U.S. Appl. No. 11/396,199, filed Mar. 30, 2006 titled "Dispersion Using Inter-metallic Materials".

U.S. Appl. No. 12/095,463, filed May 29, 2008 titled "Chalcogenide Solar Cell".

Yasuto Miyazawa and G. M. Pound, Homogeneous Nucleation of Crystalline Gallium From Liquid Gallium, Journal of Crystal Growth 23 (1974) 45-57.

L. Bosio and C. G. Windsor, Observation of a Metastability Limit in Liquid Gallium, Physical Review Letters, vol. 35, No. 24, Dec. 15, 1975.

Di Cicco, Andrea, Phase Transitions in Confined Gallium Droplets, Physical Review Letters (1998), 81(14), 2942-2945. Publisher: American Physical Society.

Poloni, R.; De Panfilis, S.; Di Cicco, A.; Pratesi, G.; Principi, E.; Trapananti, A.; Filipponi, A., Liquid gallium in confined droplets under high-temperature and high-pressure conditions, Physical Review B 71. 184111 (2005).

Di Cicco, A.; Fusari, S.; Stizza, S., Phase transitions and undercooling in confined gallium, Philosophical Magazine B: Physics of Condensed Matter: Statistical Mechanics, Electronic, Optical and Magnetic Properties (1999), 79(11/12), 2113-2120. Publisher: Taylor & Francis Ltd.

Heyding, R. D.; Keeney, W.; Segel, S. L., Metastable phases in gallium dispersions, Journal of Physics and Chemistry of Solids (1973), 34(1), 133-6.

Lee, Y.; Wang, T.; Liu, Y.; AO, J.; Li, H.; Sato, H.; Nishino, K.; Naoi, Y.; Sakai, S., Fabrication of high-output-power A1GaN-based UV-light-emitting diode using a Ga droplet layer, Japanese Journal of Applied Physics, Part 2: Letters (2002), 41(10A), L1037-L1039.

Schwarcz, D.; Nakahara, S.; Ohring, M., TEM observations of early nucleation and growth stages in aluminum films on liquid gallium droplets, Thin Solid Films (1994), 245(1-2), 260-6.

Karpov, S. Y.; Bord, O. V.; Talalaev, R. A.; Makarov, Y. N., Gallium droplet formation during MOVPE and thermal annealing of GaN, Materials Science & Engineering, B: Solid-State Materials for Advanced Technology (2001), B82(1-3), 22-24.

Berty, J.; David, M. J.; Lafourcade, L.; Defrain, A., Electron diffraction study of the supercooling of very small gallium droplets, Scripta Metallurgica (1976), 10(7), 645-8.

Huang, J. B.; Fei, G. T.; Shui, J. P.; Cui, P.; Wang, Y. Z., Preparation and internal friction of nanoscale gallium droplets, Physica Status Solidi A: Applied Research (2002), 194(1), 167-172.

U.S. Appl. No. 11/290,633 titled "Metallic Dispersion" filed Mar. 15, 2005 (NSL-019B).

Freeman et al., Ag-Clad Au Nanoparticles: Novel Aggregation, Optical, and Surface-Enhanced Raman Scattering Properties J. Phys. Chem., vol. 100, 1996, pp. 718-724.

Iset, Inc. Website (http://isetinc.com/cigs.html) from Feb. 04, 2003, available from www.archive.org . 2 pages.

Kronik, L. et al. "Interface redox engineering of Cu(In,Ga)Se2 — based solar cells: oxygen, sodium, and chemical bath effects" Thin Solic Films, v. 361-362, p. 353-359. (2000).

Office Action from U.S. Appl. No. 11/081,163.
Office Action from U.S. Appl. No. 10/782,017.
Office Action from U.S. Appl. No. 11/290,633.
Office Action from U.S. Appl. No. 11/361,522.
Office Action from U.S. Appl. No. 11/361,498.
Office Action from U.S. Appl. No. 11/361,433.
Office Action from U.S. Appl. No. 11/361,521.
Office Action from U.S. Appl. No. 11/361,497.
Office Action from U.S. Appl. No. 11/361,515.
Office Action from U.S. Appl. No. 11/361,523.
Office Action from U.S. Appl. No. 11/361,103.
Office Action from U.S. Appl. No. 11/361,688.
Office Action from U.S. Appl. No. 11/362,266.
Office Action from U.S. Appl. No. 11/395,438.
Office Action from U.S. Appl. No. 11/395,426.
Office Action from U.S. Appl. No. 11/395,668.
Office Action from U.S. Appl. No. 11/933,375.

* cited by examiner

PHOTOVOLTAIC THIN-FILM CELL PRODUCED FROM METALLIC BLEND USING HIGH-TEMPERATURE PRINTING

CROSS-REFERENCE TO RELATED APPLICATION

This application is a continuation-in-part of and claims priority to commonly-assigned, co-pending application Ser. No. 10/782,017 entitled SOLUTION-BASED FABRICATION OF PHOTOVOLTAIC CELL, filed Feb. 19 2004, the entire disclosures of which are incorporated herein by reference.

FIELD OF THE INVENTION

This invention is related to photovoltaic cells and more particularly to fabrication of IB-IIIA-VIA active layers for such cells.

BACKGROUND OF THE INVENTION

Low-cost production of solar cells on flexible substrates using printing or web coating technologies is promising highly cost-efficient alternative to traditional silicon-based solar cells. Recently, solar cells fabricated from alloys of copper (Cu) and indium (In) with selenium (Se) or sulfur (S) have been developed. Such solar cells (known as CIGS cells) have been produced using a variety of approaches, including sputtering, evaporation, and chemical vapor deposition. However, vacuum-based deposition systems such as sputtering and evaporation can only control the stoichiometric ratio of co-deposited materials with high-cost, low-speed processes. This limitation severely impacts production of solar cells where active layer composition must be tightly controlled. For example, the synthesis of a high-performance CIGS active layer is only possible within a narrow ratio of copper to indium and/or gallium. Co-evaporation or co-sputtering of the individual CIGS elements requires controlled coordination of the deposition rates in a manner that is uniform both spatially across a substrate and from run to run. It is difficult to deposit uniform films on large areas using coincident vapor phase processes. Furthermore, deposition processes such as sputtering and evaporation typically result in less efficient materials utilization, as deposited material is also transported from the source target to chamber walls or shields rather than just the substrate.

Thus, there is a need in the art for an alternative route in the fabrication of CIGS active layers that overcomes the above disadvantages.

BRIEF DESCRIPTION OF THE DRAWINGS

Embodiments of the present invention can be readily understood by considering the following detailed description in conjunction with the accompanying drawings, in which.

DESCRIPTION OF THE SPECIFIC EMBODIMENTS

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

According to embodiments of the present invention, the metallic components of a IB-IIIA-VIA photovoltaic cell active layer may be directly coated onto a substrate by using relatively low melting point (e.g., less than about 500° C.) metals such as indium and gallium. Specifically, CI(G)S thin-film solar cells may be efficiently and reproducibly fabricated directly from a metallic solution by blending one or more molten group IIIA metals with solid nanoparticles containing group IB and (optionally) group IIIA metals. The molten mixture may be coated onto a thin film substrate in the molten state, e.g., using coating techniques such as hot-dipping, hot microgravure and/or air-knife coating. After coating, the substrate may be cooled and annealed in a sulfur-containing or selenium-containing atmosphere.

It should also be understood that group IB, IIIA, and VIA elements other than Cu, In, Ga, Se, and S may be included in the description of the IB-IIIA-VIA alloys described herein, and that the use of a hyphen ("-" e.g., in Cu—Se or Cu—In—Se) does not indicate a compound, but rather indicates a coexisting mixture of the elements joined by the hyphen. Where several elements can be combined with or substituted for each other, such as In and Ga, or Se, and S, in embodiments of the present invention, it is not uncommon in this art to include in a set of parentheses those elements that can be combined or interchanged, such as (In, Ga) or (Se, S). The descriptions in this specification sometimes use this convenience. Finally, also for convenience, the elements are discussed with their commonly accepted chemical symbols. Group IB elements suitable for use in the method of this invention include copper (Cu), silver (Ag), and gold (Au). Preferably the group IB element is copper (Cu). Group IIIA elements suitable for use in the method of this invention include gallium (Ga), indium (In), aluminum (Al), and thallium (Tl). Preferably the group IIIA element is gallium (Ga) or indium (In). Group VIA elements of interest include selenium (Se), sulfur (S), and tellurium (Te), and preferably the group VIA element is either Se or S.

Figure 1:
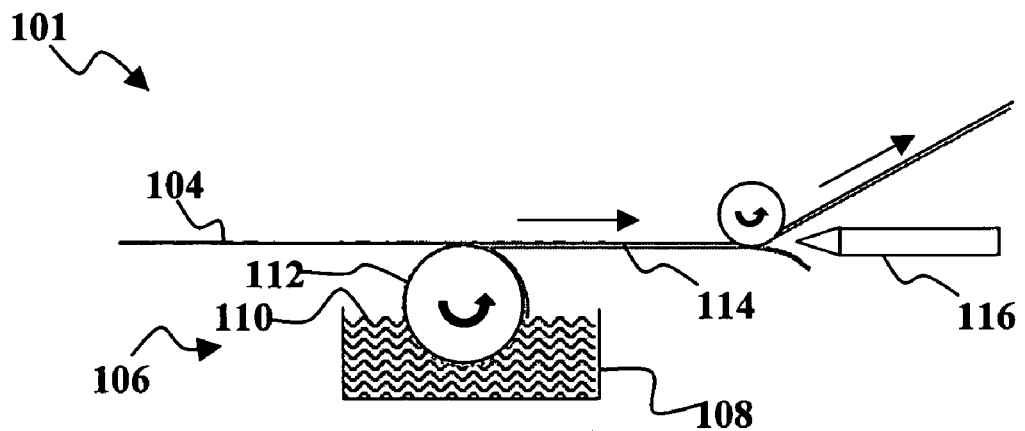
FIG. 1 is a schematic diagram illustrating fabrication of photovoltaic cells according to an embodiment of the present invention.

FIG. 1 depicts an apparatus 101 that may be used in conjunction with embodiments of the present invention. In the apparatus 101, a coating unit 106, applies a film 114 of a molten mixture 110 to a substrate 104. The molten mixture 110 includes a molten group IIIA element containing nanoparticles of a group IB element and (optionally) another group IIIA element. The substrate 104 may be a metal foil, e.g., aluminum, molybdenum or stainless steel foil, a molybdenum-coated aluminum or stainless steel foil, a molybdenum-coated plastic foil, or another thin flexible sheet material that can withstand processing at the temperature of the molten mixture. By way of example nanoparticles containing copper and gallium may be mixed with molten indium to form the molten mixture 110. By way of example, the molten mixture 110 may be made starting with a molten mixture of Indium and/or Gallium (commercially available, e.g., from Alfa Aesar of Ward Hill, Mass.). Copper nanoparticles may then be added to the molten mixture. Copper nanoparticles are available commercially, e.g., from Materials Modification Inc., of Fairfax, Va., or such nanoparticles can be produced using any of a variety of well-developed techniques, including but not limited to (i) the electro-explosion of copper wire, (ii) mechanical grinding of copper particles for a sufficient time so as to produce nanoparticles, or (iii) solution-based synthesis of copper nanoparticles from organometallic precursors. Alternatively, the temperature of a Cu—Ga—In mixture may be adjusted (e.g. cooled) until a solid forms. The solid may be ground at that temperature until small nanoparticles (e.g., less than 5 nm) are present. Selenium and/or sulfur may optionally be added to the molten mixture 110, and/or the coating 114 before, during or after coating the substrate 104.

By way of example the coating unit 6 may be a hot microgravure coater having a vat 108 of the molten mixture 110 and a microgravure roller 112. The vat 108 may be heated by a heater (not shown) to keep the mixture in the molten state. For example, indium has a melting point of about 156° C. The heater preferably keeps the molten mixture 110 at or above this temperature. The roller 112 contacts both the molten mixture 110 and a surface of the substrate 104. The roller 112 may include indentations that collect measured portions of the molten mixture from the vat 108 as the roller 112 rotates. The roller 112 rotates such that, at the point of contact with the substrate 104, the substrate and roller surfaces are moving in opposite directions relative to each other.

In alternative embodiments of the invention the coating unit 106 may be a hot-dip deposition unit that immerses the substrate in a bath of molten metal or alloy for a specific time. Hot-dip deposition is suitable if melting temperature of the molten mixture 110 is less than that of the substrate 104, the coating 114 is not too brittle and the substrate 104 has a suitable shape (e.g., no small openings.) Such coating techniques, which are commonly used to apply coatings of tin (melting point 230° C.) and zinc (melting point 419° C.), may be readily adapted to coatings based on molten indium (melting point 156° C.). An additional advantage is that such techniques can apply coatings at very high speeds (e.g., 2000 feet per minute). Coatings as thin as 1-2 microns may be obtained with hot dip coating.

In other alternative embodiments, the coating unit 106 may include an extrusion coater or hot melt coater to cast the molten mixture. Extrusion dies in an extrusion coater can form a free film that rapidly cools to form the coating 114 as a thin solid film that can subsequently be laminated to the substrate 104. An advantage of the free film approach is that the coating 114 may be processed to reduce its thickness and improve uniformity before it is laminated to the substrate 104. Alternatively, the substrate 104 may be backed by a cooled roll so that the coating 114 rapidly solidifies on the substrate 104.

In yet another alternative embodiment, the coating unit 106 may be a plasma spray coater. The plasma spray process involves the spraying of molten or heat softened material onto a surface to provide a coating. Material in the form of powder is injected into a very high temperature plasma flame, where it is rapidly heated and accelerated to high velocity. The hot material impacts the substrate surface and rapidly cools forming a coating. This plasma spray process carried out correctly is called a "cold process" as the substrate temperature can be kept low during processing avoiding damage, metallurgical changes and distortion to the substrate material.

The apparatus 101 may include a doctor blade 116 to doctor the coating 114 to a desired thickness, e.g., between 1-10 microns, preferably between about 1 micron and about 4 microns thick. The doctor blade 116 may be a solid blade or an air knife having a gas manifold with a plurality of nozzles that direct a high velocity stream of air or other gas at the coating 114 on the substrate 104. Such an air knife may doctor the coating 114 to the desired thickness with a sharp air jet.

Some high-volume batch processes for coating the substrate with the molten mixture, e.g., hot-dipping, could potentially coat both sides of a substrate at one time. However, it may be desirable to primarily coat only one side, since double-sided coating can result in waste of valuable components of the molten mixture, e.g., indium. To avoid such waste, two substrates may be temporarily attached together "back-to-back" to form a dual substrate having, in effect, two front sides. The dual substrate may then be wound into a coil and coated such that both front surfaces get coated while the back surfaces do not. Preferably, the substrates are attached in a manner that allows them to be separated from each other after processing. By way of example the substrates may be attached with a low-strength adhesive or electrostatic film applied to the back side of one or both substrates. Alternatively, an edge where the two substrates join may be sealed, e.g., with a tape, so that the molten mixture cannot reach the back sides during processing. Processing the substrate in this fashion wastes less of the molten mixture and may increase the area of the substrate that can be coated at one time.

Additional processing of the coating 114 may take place before or after the coating cools to solidify. Such additional processing may include exposure to a vapor containing one or more elements of group VIA to complete the IB-IIIA-VIA coating. For example, the coating 114 may be exposed to selenium vapor to selenize a Cu—In—Ga coating to form a Cu—In—Ga—Se alloy. The alloy may have the general formula $CuIn_{1-x}Ga_x(S, Se)_2$, where x is between 0 and 1. By way of example the stoichiometric ratio of copper to indium may be about 0.9. Alternatively, the coating 114 may be exposed to a vapor containing hydrogen selenide ($H_2Se$) or hydrogen sulfide ($H_2S$).

As set forth above, the molten mixture includes a low-melting point metal of group IB (e.g., indium and/or gallium) and particles containing elements of group IIIA and/or IB, e.g., copper and gallium. The particles may be between about 1 nanometer and about 1 micron in size, more preferably between 1 nm and 100 nm, and most preferably between 1 nm and 40 nm. The decreased particle size can significantly lower both the melting point and the sintering temperature required, especially below 10-20 nm (see e.g., C R M Wronski, "The Size Dependence of the Melting point of Small Particles of Tin" in *the British Journal of Applied Physics vol.* 18, *No.* 12, (December 1967) pp 1731-1737, IOP Publishing, Bristol, UK; L. H. Allen, "Nanocalorimetry Studies of Materials: Melting Point Depression and Magic Nanostructures" NNUN Abstracts 2002/Materials, Physics, Processes & Characterization, pp 40; Zhang et al., 2000. "Size-dependent melting point depression of nanostructures: Nanocalorimetric measurements." Phys. Rev. B 62 (15): 548-557; Lisecki et al. 2000. "Annealing Process of Anisotropic Copper Nanocrystals." 2. Rods. Langmuir 16: 8807-8808).

Generally, reduction in the melting point is inversely proportional to the particle radius, i.e., the smaller the nanoparticles, the lower the melting point. Smaller particles also tend to pack closer together and make better contact with each other. Reduction in size from bulk material to particles in about the 10-40 nm regime can already show significant differences in melting point and other altered physical and chemical properties. With much smaller particle sizes, e.g. in the nanometer size range, the surface area of particles will increase and nanoparticles will be in intimate contact with each other. In addition, in the nanometer size range, the reactivity of the particles and interaction between nanoparticles will be enhanced. This may help particles fuse together much easier thus enhancing the cohesion of the resulting CIGS layer (W. H. Qi, et al. in "China—EU Forum on Nanosized Technology" Beijing, P.R. China. December 2002. pp 86-92). This promotes coalescence between neighboring particles during sintering.

The sizes of the nanoparticles may be distributed over a relatively narrow range, e.g. with the majority of particles of a given type being within about 40% of an average particle size for that type. Note that for a molten mixture containing particles of different chemical types, e.g., different elemental metals, or different binary combinations, the different types of particles may have different average sizes so that the particles all melt at about the same temperature. By appropriately adjusting the particle size distribution amongst the particles of different materials in the mixture, it is possible for all the particles to melt at about the same temperature during sintering and yield more uniform crystalline phases. This enhances the electronic properties of the crystals in the resulting CIGS film. By contrast, in the prior art, $CuInSe_2$ powders generated, e.g., by a milling or nebulizing process to create powder precursors have typically contained a mixture of both small and large particles, resulting in a relatively broad size distribution. The presence of such a broad size distribution results in poor film formation. In particular, smaller particles tend to melt first while big particles remain unmelted. Further, particles of different sizes can non-uniformly distribute within a film. This heterogeneity leads to defects in film growth, decreases the uniformity and size of crystal grains, and negatively impacts the electronic properties (e.g., resistivity, bandgap, and carrier transport) of the CIGS layer upon incorporation into a photovoltaic device such as a solar cell.

Therefore, according to embodiments of the present invention, the nanoparticles (e.g., elemental metal nanoparticles, quantum nanoparticles, or metallic nanoparticles) in the molten mixture may be about 1-nm to about 100-nm in diameter. The nanoparticles may have a substantially uniform size distribution, characterized by an average nanoparticle size D. For example, the nanoparticles may have sizes within about 40% of D. If the average particle size is less than about 5 nm, then the variation can be bigger, e.g., between about 1 nm and about 2 nm. In this case, the resulting range of melting points is still sufficiently small to be considered to have a narrow particle size distribution. By way of example, the particles in the liquid may include Cu with In or Ga and Se or S in a stoichiometric ratio of approximately $CuIn_{1-x}Ga_x(S, Se)_2$, where x is between 0 and 1.

Methods to make nanoparticles of the desired materials having the desired narrow particle size distribution include controlling the reaction conditions under which the nanoparticles are made or using size-selective precipitation and/or other techniques such as ultrafiltration. Nanoparticles in different categories may be incorporated into the molten mixture 110. These categories include but are not limited to: (1) Ternary nanoparticles such as $CuInSe_2$ or CuInGa nanoparticles; (2) Binary nanoparticles such as CuSe and $In_2Se_3$ nanoparticles; (3) Elemental metallic nanoparticles such as Cu and In nanoparticles; (4) Metal halides dissolved in chelating agents; and (4) Metal salts. Other techniques for forming nanoparticles include includes laser ablation, mechanical milling, grinding, nucleation from vapor, exploding wires by electrical current surge, thermal treatment, sonolysis, pulse radiolysis, electrochemical reduction or chemical reduction.

Nanoparticles may or may not melt during deposition of the molten mixture 110 to form the film 114. Subsequent annealing steps (either before and optionally after selenization) can improve the microstructure of the grains in the film 114 through recrystallization and other heat-driven processes. As a result, copper atoms can be effectively and widely dispersed in the annealed film even in the absence of prior Cu nanoparticle melting.

Therefore, in a preferred embodiment of the invention, Cu nanoparticles may be added to the molten In (and optionally molten Ga) but without melting the nanoparticles. Instead the nanoparticles may be distributed throughout the molten material during the initial deposition of the film 114. Then, during a later annealing step, the film can be heated to a temperature sufficient to cause Cu atoms to diffuse and be more widely distributed through the material of the film 114.

By way of example, after deposition, the film 114 (e.g., a CIGS film) may be annealed for up to 30 minutes at a temperature of about 150-300° C. After annealing, the film may optionally be exposed to selenium vapor at about 300-500° C. for about 30-45 minutes to ensure the proper stoichiometry of Se in the film. Both of these steps may improve the microstructure and increase the grain size of the resulting CIGS layer.

Photovoltaic Devices

Figure 2:
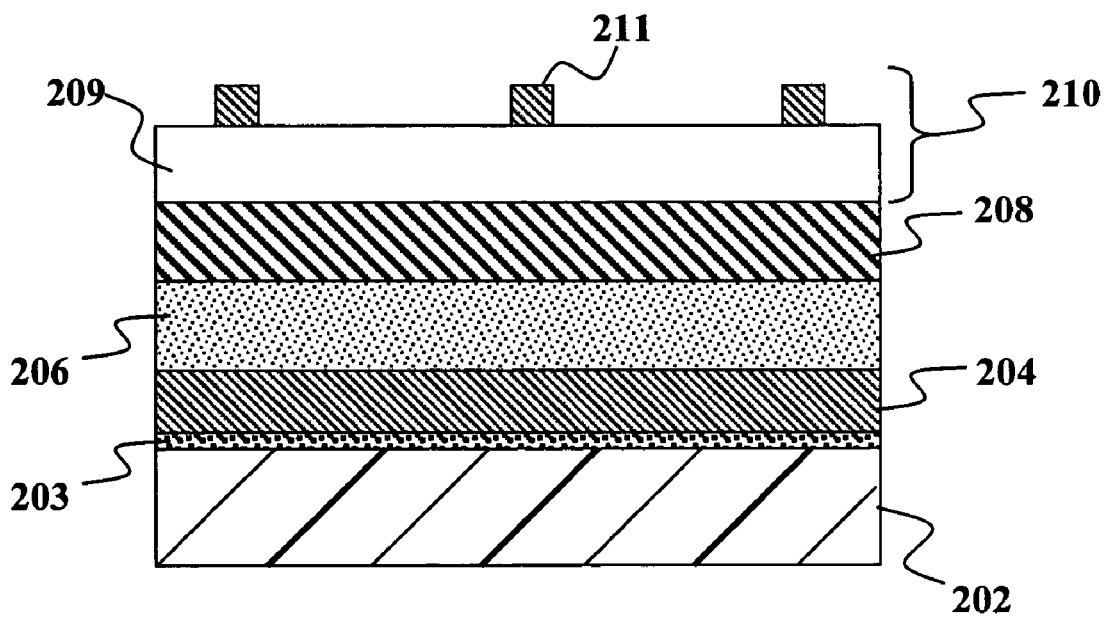
FIG. 2 is a schematic diagram of a photovoltaic cell according to an embodiment of the present invention.

A IB-IIIA-VIA alloy layer fabricated as described above can be used in the active layer of photovoltaic cell, e.g., of the type shown in FIG. 2. The solar cell 200 generally includes a substrate or base layer 202, a base electrode 204, a IB-IIIA-VIA layer 206, a window layer 208, and a transparent electrode 210. The base layer 202 may be made from a thin flexible material suitable for roll-to-roll processing. By way of example, the base layer may be made of a metal foil, such as titanium, a polymer such as polyimide or a metallized plastic. The base electrode 204 is made of an electrically conducive material. By way of example, the base electrode 204 may be a layer of stainless steel or molybdenum, e.g., about 0.5 microns to about 1 micron thick.

By way of example, and without limitation, the IB-IIIA-VIA layer 206 may include material of the general formula $CuIn_{1-x}Ga_x(S \text{ or } Se)_2$. The IB-IIIA-VIA layer 206 may be fabricated by depositing a film of a molten mixture, e.g., roughly 1 to 10 microns thick on the base electrode 204. The film may be cooled to solidify the IB-IIIA-VIA layer 206. The IB-IIIA-VIA layer 206 may be about 1 micron to about 4 microns thick after cooling. By using a molten mixture of the type described above, the IB-IIIA-VIA layer 206 may be formed at a temperature compatible with the underlying substrate 202 and electrode 204. An optional adhesion layer 203 may facilitate bonding of the electrode 204 to the substrate 202.

After annealing, the film may optionally be exposed to selenium vapor at about 300-500° C. for about 30-45 minutes to ensure the proper stoichiometry of Se in the film. To carry out such a Se vapor exposure, the film, if deposited on a flexible substrate, can be wound into a coil and the coil can be coated so that the entire roll is exposed at the same time, substantially increasing the scaleability of the Se vapor exposure process through such a high-volume batch process, e.g., as described above.

The window layer 208 is typically used as an interface between the bandgaps of the different materials making up the IB-IIIA-VIA layer 206. By way of example, the window layer may include cadmium sulfide (CdS), zinc sulfide (ZnS), or zinc selenide (ZnSe) or some combination of two or more of these. Layers of these materials may be deposited, e.g., by chemical bath deposition, typically to a thickness of about 50 nm to about 100 nm.

The transparent electrode 210 may include a transparent conductive oxide layer 209, e.g., zinc oxide (ZnO) or aluminum doped zinc oxide (ZnO:Al), which can be deposited using any of a variety of means including but not limited to sputtering, evaporation, CBD, electroplating, CVD, PVD, ALD, and the like. If the substrate is flexible and the deposition technique is ALD or CBD or the like, a coiled/wound flexible substrate can be exposed so that the entire roll is processed at one time, e.g., as described above. The transparent electrode 210 may further include a layer of metal (e.g., Ni, Al or Ag) fingers 211 to reduce the overall sheet resistance.

An optional encapsulant layer (not shown) provides environmental resistance, e.g., protection against exposure to water or air. The encapsulant may also absorb UV-light to protect the underlying layers. Examples of suitable encapsulant materials include one or more layers of polymers, such as tetrafluoroethylene-hexafluoropropylene-vinylidenflouride-copolymer (THV), polyethylene terephthalate (PET), ethylene vinyl acetate (EVA), and/or Mylar®. Mylar is a registered trademark of E. I. du Pont de Nemours and Company of Wilmington, Del. Inorganic materials, such as glass and plastic foils, metalized plastic foils, and metal foils may also be used for the encapsulant layer. The encapsulant layer may also include nitrides, oxides, oxynitrides or other inorganic materials. Alternatively, the encapsulants may include Tefzel® (DuPont), tefdel, thermoplastics, polyimides, polyamides, nanolaminate composites of plastics and glasses (e.g. barrier films), and combinations of the above. For example, a thin layer of (relatively expensive) EVA/polyimide can be laminated to thick layer of (much less expensive) PET.

Embodiments of the present invention provide for low-cost, high-volume production of large area photovoltaic devices. Further, in contrast to prior solution-based approaches that have focused on lower temperature CIGS processing, embodiments of the present invention utilize higher-temperature CIGS processing, e.g., in a temperature range of about 150-250° C., with hot-melt coating equipment, and enable direct deposition of a thin film from a molten metallic paste.

Furthermore, embodiments of the present invention are compatible with roll-to-roll manufacturing of photovoltaic cells and modules that can be readily scaled up to high production volumes.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. In the claims that follow, the indefinite article "A", or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. A method for forming an active layer coating, the method comprising the steps of:
    forming a molten mixture of one or more metals of group IIIA and metallic nanoparticles containing elements of group IB;
    subsequently depositing the molten mixture on a substrate to form a film; and
    processing the film in one or more steps to form a photovoltaic absorber layer.

2. The method of claim 1 wherein the nanoparticles are between about 1 nanometer and about 1 micron in size.

3. The method of claim 2 wherein the nanoparticles are between about 1 nanometer and about 500 nanometers in size.

4. The method of claim 3 wherein the nanoparticles are between about 1 nanometer and about 100 nanometers in size.

5. The method of claim 4 wherein the nanoparticles are between about 1 nanometer and about 50 nanometers in size.

6. The method of claim 1 wherein the nanoparticles have a substantially uniform size distribution characterized by an average particle size D.

7. The method of claim 6 wherein, if D is greater than about 5 nm, the nanoparticles have sizes within about 40% of D.

8. The method of claim 6 wherein, if the average particle size is less than about 5 nm, the nanoparticles have sizes within about 2 nm of D.

9. The method of claim 1 wherein the molten mixture includes one or more metals with melting points of less than about 525° C.

10. The method of claim 1 wherein forming the molten mixture includes forming the nanoparticles by laser ablation, mechanical milling, grinding, nucleation from vapor, exploding wires by electrical current surge, thermal treatment, sonolysis, pulse radiolysis, electrochemical reduction or chemical reduction.

11. The method of claim 1, wherein depositing the molten mixture includes microgravure coating the molten mixture onto a surface of the substrate.

12. The method of claim 1, wherein depositing the molten mixture includes hot-dip coating the molten mixture onto the substrate.

13. The method of claim 1 wherein depositing the molten mixture includes extruding the molten mixture to form a film.

14. The method of claim 13 further comprising laminating the film to the substrate.

15. The method of claim 1 wherein depositing the molten mixture includes plasma spray coating the molten mixture onto the substrate.

16. The method of claim 1, further comprising adjusting a thickness of the film formed from the molten mixture.

17. The method of claim 16 wherein adjusting a thickness of the film formed from the molten mixture includes doctoring the film.

18. The method of claim 17 wherein doctoring the film includes the use of an air knife.

19. The method of claim 1 wherein the group IB element is copper (Cu), and one or more metals of group IIIA include indium and (optionally) gallium.

20. The method of claim 19 wherein a stoichiometric ratio of copper to indium in the film is about 0.9.

21. The method of claim 19 wherein the In and (optionally) Ga are molten and wherein the Cu nanoparticles are added to the molten In (and optionally molten Ga) but without melting the Cu nanoparticles.

22. The method of claim 1, further comprising cooling the substrate to rapidly solidify the coating on the substrate.

23. The method of claim 1 further comprising melting the nanoparticles in the molten mixture.

24. The method of claim 1 further comprising maintaining the molten mixture at a sufficiently low temperature that the nanoparticles do not melt in the molten mixture.

25. The method of claim 1 further comprising annealing the film formed from the molten mixture.

26. The method of claim 25 wherein the group IB element is copper and annealing the film includes heating the film to a temperature sufficient to cause Cu atoms to diffuse through the material of the film.

27. The method of claim 1 wherein at least some of the nanoparticles are ternary nanoparticles.

28. The method of claim 1 wherein at least some of the nanoparticles are binary nanoparticles.

29. The method of claim 1 wherein at least some of the nanoparticles are elemental nanoparticles.

30. The method of claim 1 wherein at least some of the nanoparticles are metal halide nanoparticles.

31. The method of claim 1 wherein at least some of the nanoparticles are metal salt nanoparticles.

32. The method of claim 1 wherein at least some of the nanoparticles melt during deposition of the molten mixture.

33. The method of claim 1 wherein the nanoparticles do not melt during deposition of the molten mixture.

34. The method of claim 1 further comprising annealing the film to form an annealed film and then selenizing the annealed film.

35. The method of claim 1 further comprising selenizing the film to form a selenized film and then annealing the selenized film.

36. The method of claim 1 wherein processing comprises exposing the film to group VIA vapor.

37. The method of claim 1 wherein processing comprises heating the film in a sulfur-containing or selenium-containing atmosphere.

38. The method of claim 1 wherein the substrate comprises at least one of the following: aluminum, molybdenum, stainless steel, a molybdenum-coated aluminum or stainless steel foil, a molybdenum-coated plastic foil, or another thin flexible sheet material that can withstand processing at the temperature of the molten mixture.

39. The method of claim 1 wherein processing comprises heating the film in a hydrogen selenide ($H_2Se$) or hydrogen sulfide ($H_2S$).

40. A method for forming an active layer coating, the method comprising the steps of:

forming a molten mixture of one or more metals of group IIIA and metallic nanoparticles containing elements of group IB;

subsequently depositing the molten mixture on a substrate to form a film;

processing the film in one or more steps to form a photovoltaic absorber layer; and incorporating one or more elements of Group VIA into the film.

41. The method of claim 40 wherein incorporating one or more elements of group VIA into the film includes exposing the film to a vapor containing selenium, sulfur, $H_2S$ or $H_2Se$.

42. The method of claim 41 wherein the group VIA element is selenium (Se) or sulfur (S).

43. The method of claim 40 wherein the group VIA element is selenium (Se) or sulfur (S), the group IB element is cooper (Cu), and one or more metals of group IIIA includes indium (In) and (optionally) gallium (Ga) and wherein a stoichiometric ratio of the Cu, In and Se or S in the active layer coating is approximately $CuIn_{1-x}Ga_x(S \text{ or } Se)_2$, where x is between 0 and 1.

44. A method for forming an active layer coating, the method comprising the steps of:

forming a molten mixture of one or more metals of group IIIA and metallic nanoparticles containing elements of group IB;

subsequently depositing the molten mixture on a substrate to form a film; and processing the film in one or more steps to form a photovoltaic absorber layer;

wherein processing comprises annealing the film to form an annealed film and then exposing the annealed film to group VIA vapor.

* * * * *